(12) United States Patent
Park et al.

(10) Patent No.: US 11,871,178 B2
(45) Date of Patent: Jan. 9, 2024

(54) ELECTRONIC DEVICE COMPRISING SPEAKER ASSEMBLY

(71) Applicant: Samsung Electronics Co., Ltd., Suwon-si (KR)

(72) Inventors: Jiwoong Park, Suwon-si (KR); Hyeonjoong Kim, Suwon-si (KR); Sungeun Park, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 43 days.

(21) Appl. No.: 17/649,306

(22) Filed: Jan. 28, 2022

(65) Prior Publication Data
US 2022/0232312 A1    Jul. 21, 2022

Related U.S. Application Data

(63) Continuation of application No. PCT/KR2020/003056, filed on Mar. 4, 2020.

(30) Foreign Application Priority Data

Jul. 29, 2019 (KR) .................. 10-2019-0092037

(51) Int. Cl.
*H04R 1/02* (2006.01)
*G06F 3/041* (2006.01)
(Continued)

(52) U.S. Cl.
CPC ........ *H04R 1/2811* (2013.01); *A61B 5/02438* (2013.01); *G04G 17/04* (2013.01);
(Continued)

(58) Field of Classification Search
CPC ........ H04R 1/2811; H04R 1/028; H04R 1/04; H04R 2400/11; H04R 2499/11;
(Continued)

(56) References Cited

U.S. PATENT DOCUMENTS 4,244,044 A * 1/1981 Olsson ................... G04B 27/08
368/294
2009/0295596 A1* 12/2009 Downey ................. G04G 21/04
340/850

(Continued)

FOREIGN PATENT DOCUMENTS

EP          2128724 A2    12/2009
JP       2005-100312 A     4/2005
(Continued)

OTHER PUBLICATIONS

International Search Report and Written Opinion of the International Searching Authority in connection with International Application No. PCT/KR2020/003056 dated Jun. 9, 2020, 9 pages.

*Primary Examiner* — Oyesola C Ojo

(57) ABSTRACT

An electronic device comprises a housing including a window member facing a first direction, a rear housing facing a second direction that is opposite to the first direction, and a side member encompassing the space between the window member and the rear housing. The electronic device also includes a display that is visible through at least a part of the window member and a speaker assembly disposed in the space. The speaker assemble includes a speaker diaphragm. The side member includes a resonance space including a shape a recessed form in a third direction that is substantially perpendicular to the first direction or the second direction. A through hole is formed in the third direction in a part of the resonance space that is closer to the rear housing than to the window member. A part of the resonance space can be disposed so as to overlap the speaker diaphragm.

20 Claims, 10 Drawing Sheets

(51) Int. Cl.
*H04R 1/04* (2006.01)
*H04R 1/28* (2006.01)
*A61B 5/024* (2006.01)
*G04G 17/04* (2006.01)
*G04G 21/02* (2010.01)
*G06F 1/18* (2006.01)

(52) U.S. Cl.
CPC .......... *G04G 21/025* (2013.01); *G06F 3/0412* (2013.01); *H04R 1/028* (2013.01); *H04R 1/04* (2013.01); *G06F 1/181* (2013.01); *G06F 2203/04102* (2013.01); *H04R 2400/11* (2013.01); *H04R 2499/11* (2013.01); *H04R 2499/15* (2013.01)

(58) Field of Classification Search
CPC .... H04R 2499/15; H04R 9/06; H04R 1/2819; H04R 1/02; A61B 5/02438; A61B 5/01; A61B 5/02416; A61B 5/11; A61B 2562/0219; A61B 2562/0271; A61B 2562/029; A61B 5/681; A61B 5/6824; A61B 5/1172; G04G 17/04; G04G 21/025; G04G 17/00; G04G 17/02; G04G 21/00; G06F 3/0412; G06F 1/181; G06F 2203/04102; G06F 1/163; G06F 1/1643; G06F 1/1658; G06F 1/1688

See application file for complete search history.

(56) References Cited

U.S. PATENT DOCUMENTS

| | | | |
|---|---|---|---|
| 2015/0163572 A1* | 6/2015 | Weiss | H04R 1/2876 381/337 |
| 2018/0063981 A1* | 3/2018 | Park | H04R 1/023 |
| 2018/0084323 A1* | 3/2018 | Luce | H04R 9/025 |
| 2018/0227668 A1* | 8/2018 | Park | H04R 1/44 |
| 2019/0110744 A1* | 4/2019 | Zhu | A61B 5/7475 |
| 2020/0359145 A1 | 11/2020 | Kim et al. | |

FOREIGN PATENT DOCUMENTS

| | | |
|---|---|---|
| KR | 10-2014-0145068 A | 12/2014 |
| KR | 10-1612791 B1 | 4/2016 |
| KR | 10-1690524 B1 | 12/2016 |
| KR | 10-2018-0024632 A | 3/2018 |
| KR | 10-2018-0092219 A | 8/2018 |
| KR | 10-2019-0086899 A | 7/2019 |

\* cited by examiner

ELECTRONIC DEVICE COMPRISING SPEAKER ASSEMBLY

CROSS-REFERENCE TO RELATED APPLICATIONS

This application is a continuation of International Application No. PCT/KR2020/003056, filed Mar. 4, 2020, which claims priority to Korean Patent Application No. 10-2019-0092037, filed Jul. 29, 2019, the disclosures of which are herein incorporated by reference in their entirety.

BACKGROUND

1. Field

Various embodiments of the disclosure relate to an electronic device including a speaker assembly.

2. Description of Related Art

An electronic device may include a device that performs a specific function according to a program provided therein, such as a home appliance, an electronic scheduler, a portable multimedia reproducer, a mobile communication terminal, a tablet PC, an image/sound device, a desktop/laptop PC, or a vehicle navigation.

Recently, wearable electronic devices having various shapes of glasses, a watch, and the like have been developed so that the electronic devices can be used in the state of being mounted on a human body. As the use of electronic devices becomes commonplace and the electronic devices are equipped with a dustproof or waterproof structure, the number of users who engage in leisure activities in the state of wearing an electronic device is gradually increasing.

In an electronic device, a waterproof member may be disposed between components to block introduction of foreign substances or moisture from the outside. However, since a microphone hole or a speaker hole that provides a sound input/output path may be exposed or opened to the outside, an external material such as moisture may be introduced into the sound input/output path. When the moisture introduced into the sound input/output path or the like remains, it may become an obstacle in sound input/output, and the introduced moisture may corrode the internal space of the electronic device.

In an electronic device, a display device may be disposed outside the electronic device to visually provide information to a user. Demand for a miniaturized electronic device that provides a display device with high visibility is gradually increasing.

According to various embodiments of the disclosure, it is possible to provide an electronic device including a speaker assembly, wherein moisture remaining in a resonance space and a sound input/output path can be easily discharged.

According to various embodiments of the disclosure, it is possible to provide an electronic device having a reduced bezel size.

However, problems to be solved in this disclosure are not limited to those described above, and may be variously expanded without departing from the spirit and scope of this disclosure.

SUMMARY

According to various embodiments of the disclosure, an electronic device may include: a housing including a window member oriented in a first direction, a rear housing oriented in a second direction that is opposite to the first direction, and a side member surrounding a space between the window member and the rear housing, a display that is visible through at least a portion of the window member, and a speaker assembly disposed in the space and including a speaker diaphragm, wherein the side member may include a resonance space having a shape recessed from the space in a third direction that is substantially perpendicular to the first direction or the second direction, and at least one through hole provided in the third direction in a portion of the resonance space that is closer to the rear housing than to the window member, and wherein a portion of the resonance space may be disposed to overlap the speaker diaphragm when the resonance space is viewed in the third direction.

According to various embodiments of the disclosure, an electronic device may include a side member including a through hole provided therethrough, a rear housing coupled to the side member, a speaker assembly including a first surface on which a speaker diaphragm is disposed to face the through hole and a second surface facing away from the first surface, a support member coupled to the side member and provided to surround at least a portion of the speaker assembly, and a fixing member configured to press at least a portion of the speaker assembly and the support member. A resonance space may be provided between at least a portion of an inner surface of the side member and the support member.

An electronic device according to various embodiments of the disclosure may include a window member at least a portion of which is substantially transparent, a second circuit board, a touch sensor module including a touch sensor disposed under the window member, and a first bent unit extending from the touch sensor in a first bending direction and configured to electrically connect the touch sensor and the second circuit board to each other, and a display module including a display panel disposed between the touch sensor and the second circuit board, and a second bent unit extending from the display panel in a second bending direction that is different from the first bending direction and configured to electrically connect the display panel and the second circuit board to each other.

In an electronic device according to various embodiments of the disclosure, it is possible to provide a speaker structure in which a resonance space and a through hole are provided in a side member. As a result, moisture remaining in a sound input/output path can be easily discharged.

In an electronic device according to various embodiments of the disclosure, it is possible to provide a display structure in which a bent unit of a touch sensor module and a bent unit of a display module are disposed in different directions. As a result, the size of the bezel can be reduced, and thus the proportion of a visible area can be increased.

Before undertaking the detailed description below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 10B, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Figure 1:
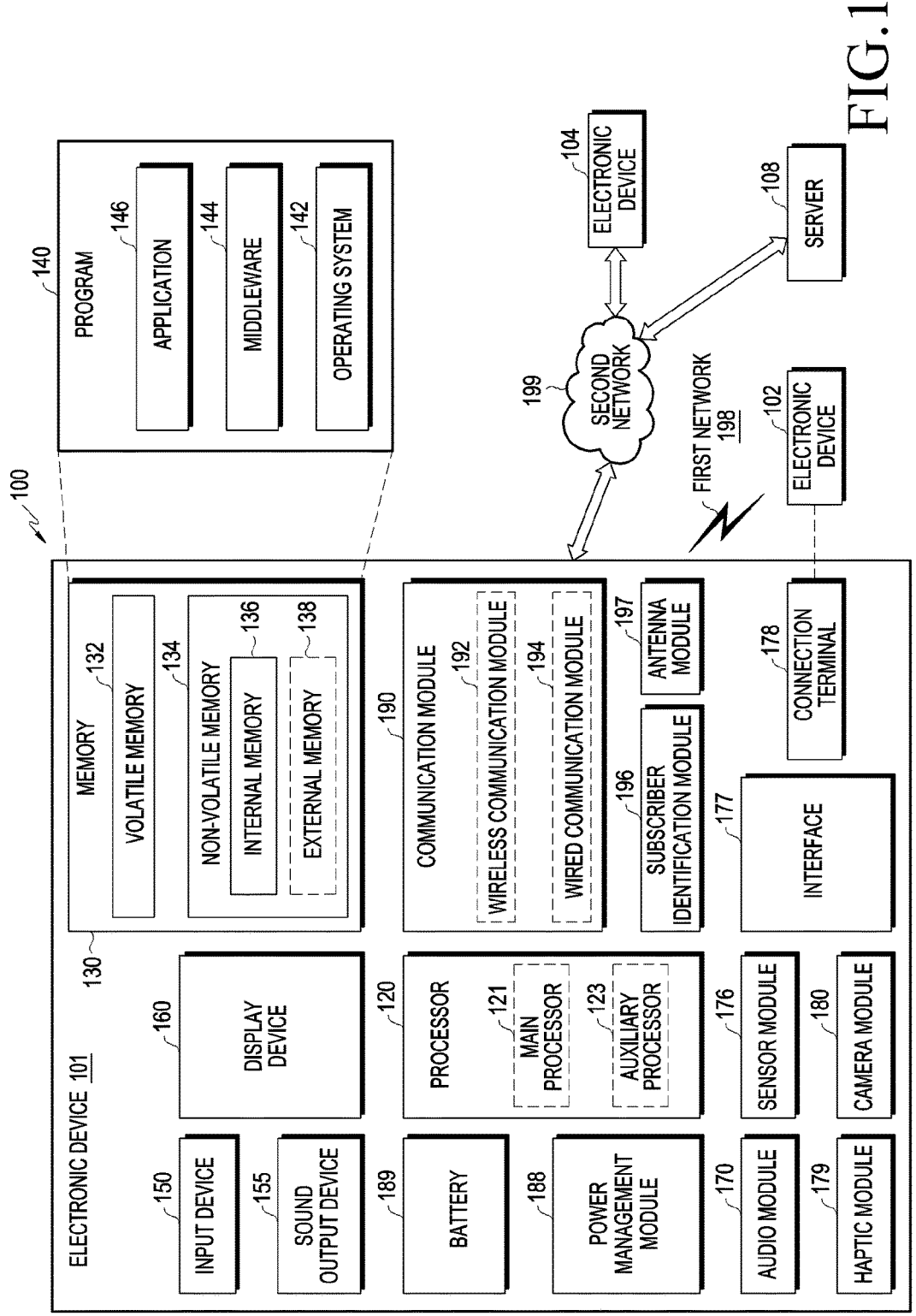
FIG. 1 is a block diagram of an illustrating an electronic device according to various embodiments of the disclosure in a network environment.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control, for example, at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active (e.g., executing an application) state. According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by a component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or an external electronic device (e.g., an electronic device 102 (e.g., a speaker or a headphone)) directly or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, an HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image and moving images. According to an embodiment, the camera module 180 may include one or more lenses, image sensors, image signal processors, or flashes.

The power management module 188 may manage power supplied to the electronic device 101. According to one embodiment, the power management module 388 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and support a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

According to various embodiments, each component (e.g., a module or a program) of the above-described components may include a single entity or multiple entities. According to various embodiments, one or more of the above-described components or operations may be omitted, or one or more other components or operations may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2A:
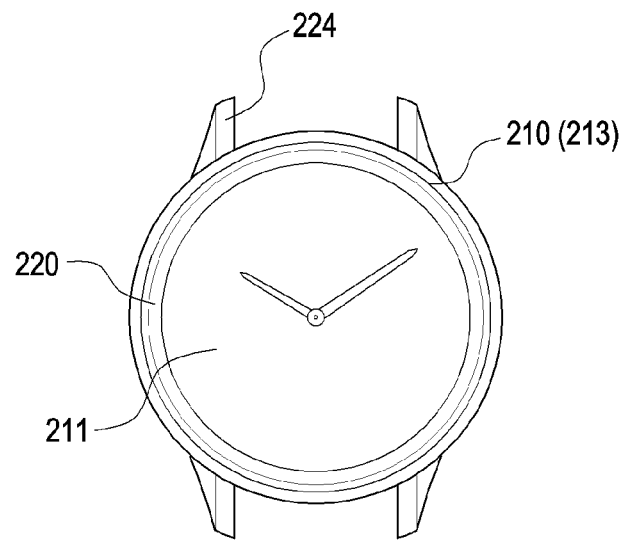
FIG. 2A illustrates a front view of an electronic device according to various embodiments of the disclosure.
Figure 2B:
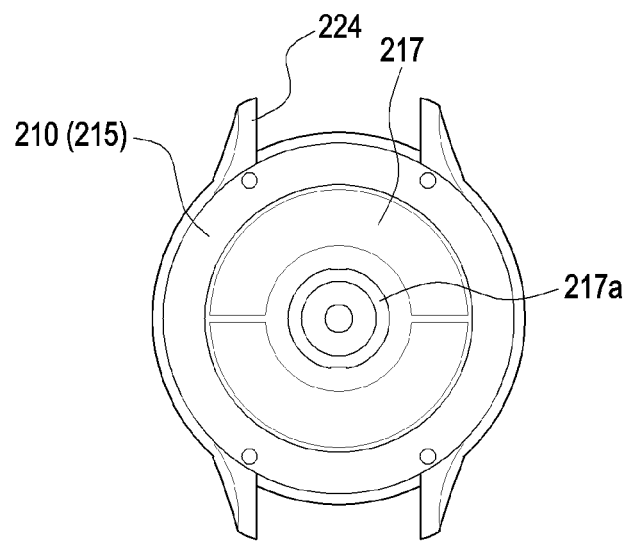
FIG. 2B illustrates a rear view of the electronic device according to various embodiments of the disclosure.

FIG. 2A illustrates a front view of an electronic device according to various embodiments of the disclosure, and FIG. 2B illustrates a rear view of the electronic device according to various embodiments of the disclosure.

An electronic device according to various embodiments of the disclosure may be a portable communication device, such as a mobile communication terminal, or a wearable electronic device that is wearable on a user's body. Hereinafter, as an electronic device according to various embodiments of the disclosure, a smartwatch will be described as an example.

Referring to FIGS. 2A and 2B, an electronic device 200 according to various embodiments of the disclosure may include a window member 211, a side member 213, a rear housing 215, and/or locking members 224.

According to various embodiments, the housing 210 may define an external appearance of the electronic device 200, and electronic components of the electronic device 200 may be disposed within the housing 210.

According to various embodiments, various circuit devices, for example, the processor 120 (e.g., an application processor (AP)), the memory 130, the input device 150, the sound output device 155, and/or the battery (e.g., the battery 370 in FIG. 5), which have been described above with reference to FIG. 1, may be disposed within the housing.

According to various embodiments, the housing 210 may include a window member 211, a side member 213, and/or a rear housing 215.

According to various embodiments, the window member 211 may be coupled to the side member 213 and may define at least a portion of the outer surface of the electronic device 200. For example, the window member 211 may be coupled to the top surface (e.g., 213b in FIG. 5) of the side member 213 using an adhesive tape or an adhesive.

According to various embodiments, the window member 211 may be made of a transparent material such as glass or resin (e.g., acrylic or polycarbonate) to provide a user with a screen output from the display device (e.g., the display device 160 of FIG. 1). For example, an analog watch-type screen may be exposed through the window member 211.

According to various embodiments, the side member 213 may be coupled to the window member 211 and the rear housing 215 and define at least a portion of the outer surface of the electronic device 200. In an embodiment, the side member 213 may be made of a highly rigid material in order to provide the electronic device 200 improved in structural stability. For example, the side member 213 may be made of a metal material. According to an embodiment of the disclosure, the side member 213 made of a metal material may be used as an antenna radiator.

According to various embodiments, the rear housing 215 may be coupled to the side member 213 and define at least a portion of the outer surface of the electronic device 200. The rear housing 215 may be made of various materials. For example, the rear housing 215 may be made of plastic.

According to various embodiments, the second plate 217 may be disposed on the rear housing 215. The second plate 217 may include at least one substantially transparent area 217a so that light generated from a light-emitting unit (e.g., the light-emitting unit 372 in FIG. 5) disposed within the housing 210 is emitted to the outside.

According to various embodiments, the bezel 220 may be provided at the edge of the window member 211. According to an embodiment, the bezel 220 may be defined as at least a portion of the window member 211 adjacent to the side member 213. According to another embodiment, the bezel 220 may be disposed at the edge of the window member 211 and coupled to the side member 213 to rotate along the edge of the window member 211. In an embodiment, the bezel 220 may be made of metal. The bezel 220 made of metal may be used as an antenna radiator.

According to various embodiments, each of the locking members 224 may be disposed to extend and protrude from the side member 213 in directions away from each other. The locking members 224 may be coupled to wearing units (not illustrated) disposed to be worn on a user's wrist. The locking members 224 may be provided with fastening grooves to which the wearing units are engaged, respectively. A plurality of fastening grooves may be provided in the side surface of the housing 210, or a fastening groove may have a closed loop shape extending along the periphery of the housing 210. The wearing units may be made of various materials (e.g., rubber, plastic, or metal).

Figure 3:
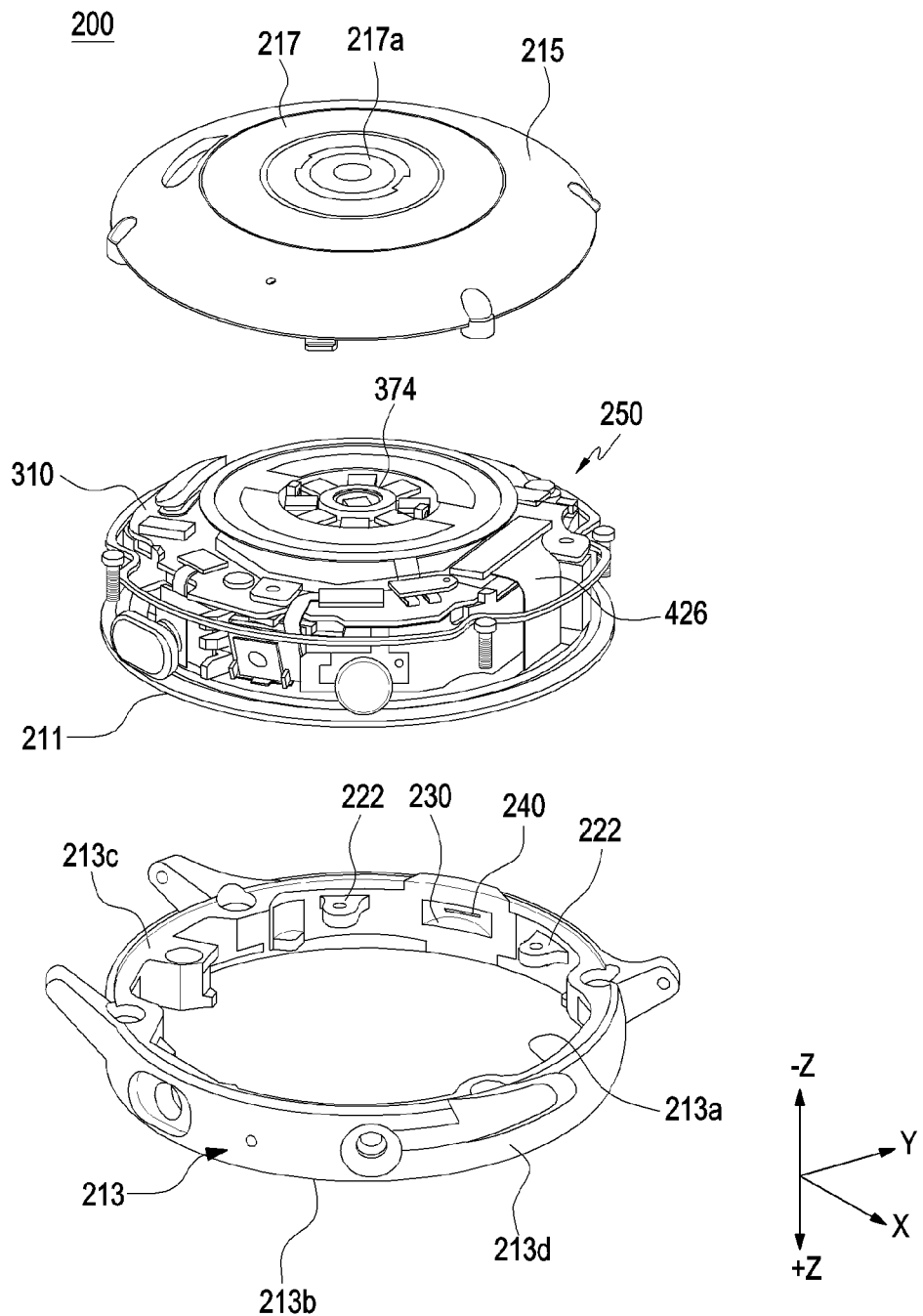
FIG. 3 illustrates an exploded perspective view of the electronic device according to various embodiments of the disclosure.

FIG. 3 illustrates an exploded perspective view of the electronic device according to various embodiments of the disclosure.

In FIG. 3, the "+Z" direction in a three-axis Cartesian coordinate system may indicate a first direction, the "−Z" direction may indicate a second direction, and the "Y" direction may indicate a third direction.

Referring to FIG. 3, the electronic device 200 may include a window member 211, a side member 213, a rear housing 215, a resonance space 230, a through hole 240, an electronic component 250, a first circuit board 310, and/or a biometric sensor 374. All or a part of the configurations of the window member 211, the side member 213, and the rear housing 215 of FIG. 3 may be the same as or similar to the configurations of the window member 211, the side member 213, and the rear housing 215 of FIGS. 2A and 2B.

According to various embodiments, the window member 211 and the rear housing 215 may be coupled to the side member 213. For example, the side member 213 may include an inner surface 213a of the side member 213, a top surface 213b of the side member 213, and a bottom surface 213c of the side member 213. At least a portion of the window member 211 may be coupled to the top surface 213b of the side member 213 via a sealing member (e.g., the sealing member 450 in FIG. 9). The rear housing 215 may be in contact with the bottom surface 213c of the side member 213 and may be coupled to the side member 213 through screw coupling.

According to various embodiments, the through hole 240 may be provided to penetrate the side member 213 from the inner surface 213a to the outer surface 213d of the same. For example, the through hole 240 may be provided in the side member 213 in a direction perpendicular to the first direction (+Z) or the second direction (−Z).

According to various embodiments, the side member 213 may be made of a material more rigid than the rear housing 215, which is injection-molded. For example, the side member 213 may be made of metal, and the rear housing 215 may be injection-molded using plastic. When the through hole 240 is provided in the side member 213 made of metal, the easiness of micro-machining may be improved compared to the case in which the through hole 240 is provided in the rear housing 215, which is injection-molded.

According to various embodiments, the through hole 240 may have various shapes. For example, in FIG. 3, the through hole 240 is illustrated as a single hole having a rectangular cross section with reference to the ZX plane. However, a plurality of holes having a circular cross section with reference to the ZX plane or a rectangular cross section with reference to the ZX plane may be provided. In addition to this, the through hole 240 may have various shapes.

According to various embodiments, an electronic component 250 on which the first circuit board 310 and the display (e.g., the display 400 in FIG. 5) are disposed may be coupled to the rear housing 215.

According to various embodiments, various components of the electronic device 200 may be disposed on the first circuit board 310. At least one of a processor (e.g., the processor 120 in FIG. 1), a memory (e.g., the memory 130 in FIG. 1), or an interface (e.g., the interface 177 in FIG. 1) may be disposed on the first circuit board 310. The processor may include, for example, one or more of a central processing unit, an application processor, a graphics processing unit (GPU), an application processor sensor processor, or a communication processor. The memory may include, for example, a volatile memory or a nonvolatile memory. The interface may include, for example, a high-definition multimedia interface (HDMI), a universal serial bus (USB) interface, an SD card interface, and/or an audio interface. The interface may electrically or physically connect, for example, the electronic device 200 to an external electronic device and may include a USB connector, an SD card/an MMC connector, or an audio connector. According to an embodiment, the processor may control various components of the electronic device 200. For example, the processor may control a touch sensor module (e.g., the touch sensor module 410 in FIG. 9), a display module (e.g., the display module 420 in FIG. 9), a speaker assembly (e.g., the speaker assembly 320 of FIG. 6B), and/or a biometric sensor 374.

According to various embodiments, the biometric sensor 374 may be disposed between the first circuit board 310 and the second plate 217 to detect the user's biometric information. For example, the biometric sensor 374 may include a heart rate monitor (HRM). The biometric sensor 374 may include a light-emitting unit 372 and a light-receiving unit (not illustrated) to detect contraction/expansion of blood vessels based on reflection of light according to a change in blood volume in the blood vessels in the skin of a human body. The processor (e.g., the processor 120 in FIG. 1) may receive an electrical signal of the biometric sensor 374 to calculate heartbeat.

Figure 4A:
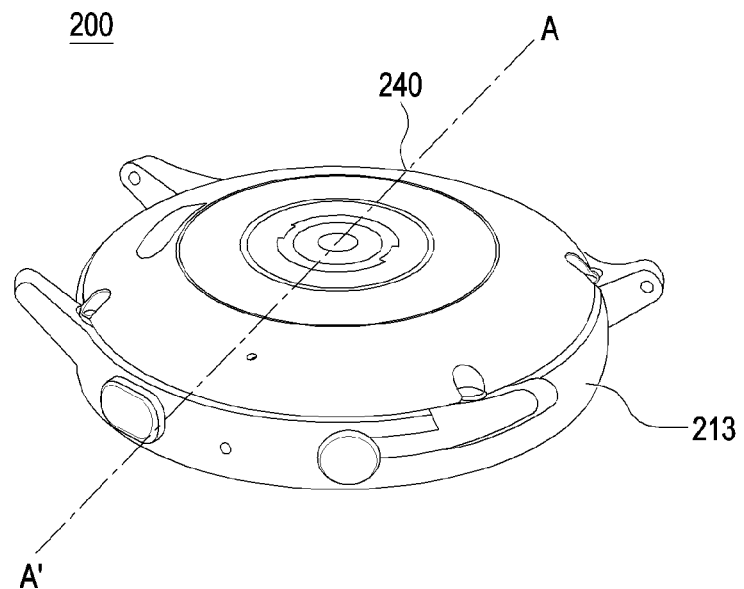
FIGS. 4A and 4B illustrate perspective views of an electronic device according to various embodiments of the disclosure.
Figure 4B:
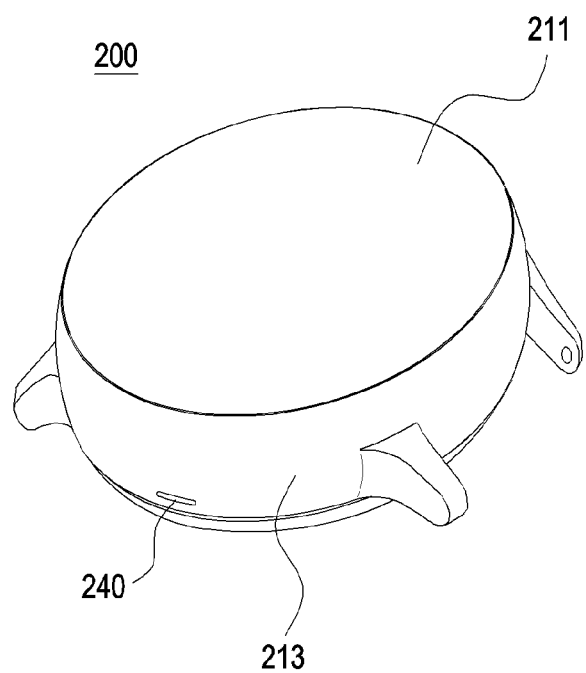
Figure 5:
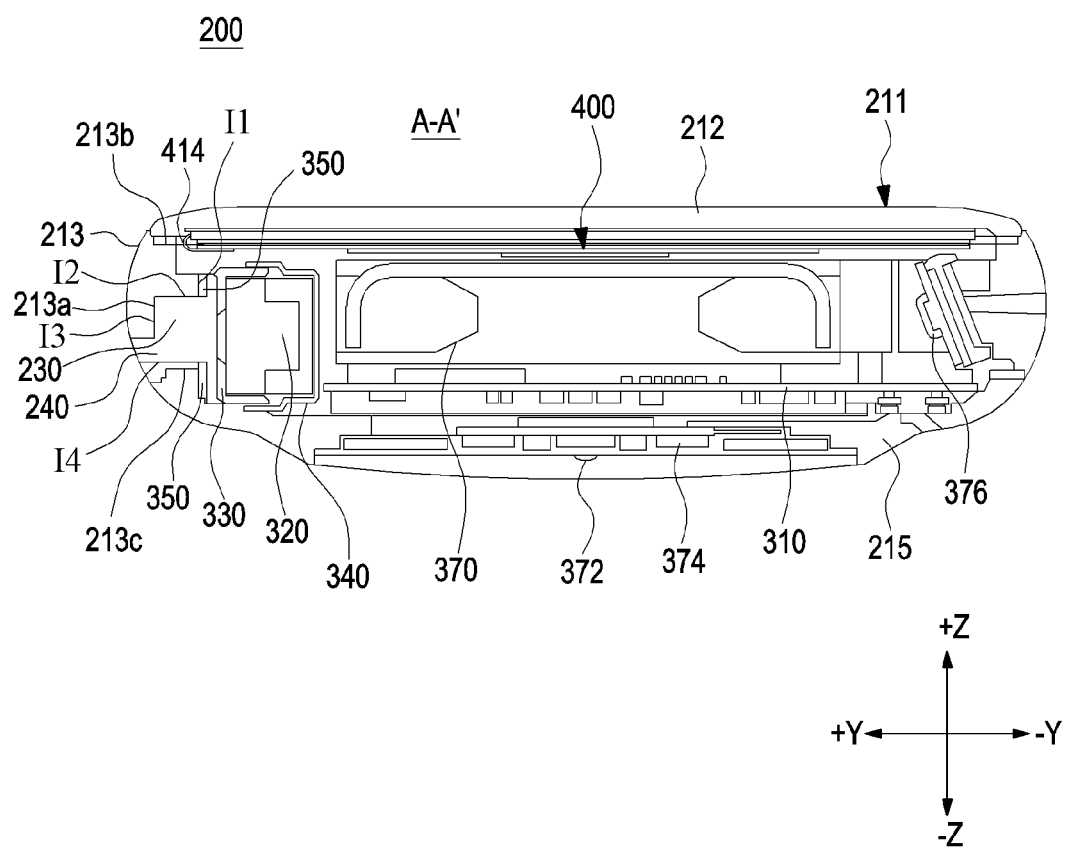
FIG. 5 illustrates a cross-sectional view of the electronic device taken along line A-A' in FIG. 4B according to various embodiments of the disclosure.

FIGS. 4A and 4B illustrate perspective views of an electronic device according to various embodiments of the disclosure. FIG. 5 illustrates a cross-sectional view of the electronic device taken along line A-A' in FIG. 4B according to various embodiments of the disclosure.

In FIG. 5, the "+Z" direction in a two-axis Cartesian coordinate system may indicate a first direction, the "−Z" direction may indicate a second direction, and the "+Y" direction may indicate a third direction.

According to FIGS. 4A, 4B and 5, an electronic device 200 may include a window member 211, a side member 213, a rear housing 215, a resonance space 230, a through hole 240, a first circuit board 310, a speaker assembly 320, a support member 330, a fixing member 340, an adhesive sheet 350, a battery 370, a light-emitting unit 372, a biometric sensor 374, and/or a microphone 376. All or a part of the configurations of the window member 211, the side member 213, the rear housing 215, the through hole 240, the first circuit board 310, the light-emitting unit 372, and the biometric sensor 374 of FIGS. 4A, 4B, and 5 may be the same as the configurations of the window member 211, the side member 213, the rear housing 215, the through hole 240, the first circuit board 310, the light-emitting unit 372, and/or the biometric sensor 374 of FIG. 3.

According to various embodiments, the speaker assembly 320 is a component that outputs sound, and may correspond to a sound output device (e.g., the sound output device 155 in FIG. 1). The speaker assembly 320 may be disposed to face the through hole 240. For example, the speaker assembly 320 may include a first surface (e.g., the first surface 320a in FIG. 6B) on which a speaker diaphragm (not illustrated) facing the through hole 240 is disposed in a third direction (the +Y direction) and a second surface 320b which is oriented in a fourth direction (the −Y direction) opposite to the first surface 320a.

According to various embodiments, the support member 330 may be disposed adjacent to the through hole 240 so as to dispose the speaker assembly 320 in the electronic device 200. The support member 330 may be provided to surround at least a portion of the speaker assembly.

According to various embodiments, the support member 330 may be coupled to the side member 213 so as to prevent the speaker assembly 320 from shaking. According to an embodiment, the support member 330 may be coupled to the inner surface 213a of the side member 213 via the adhesive sheet 350. According to another embodiment, the support member 330 may be coupled to the side member 213 via a fastening member (e.g., the fastening member 360 in FIG. 8B). According to another embodiment, the support member 330 may be coupled to the side member 213 via an adhesive sheet 350 and a fastening member (e.g., the fastening member 360 in FIG. 8B).

According to various embodiments, the through hole 240 may be provided in the side member 213 on which the speaker assembly 320 is disposed to provide a sound input/output path. In FIG. 5, since the through hole 240 is disposed in the side member 213 adjacent to the speaker assembly 320, the through hole 240 may provide a sound output path. However, the disclosure is not limited thereto, and when the through hole 240 is disposed in the side member 213 adjacent to the microphone structure, the through hole 240 may provide a sound input path. According to an embodiment, the axial direction of the through hole 240 may be perpendicular to the first surface 320a of the speaker assembly 320.

According to various embodiments, the resonance space 230 may be provided in the inner surface 213a of the side member 213. According to an embodiment, the resonance space 230 may be connected to the through hole 240. For example, the resonance space 230 may be disposed between at least a portion of the inner surface 213a of the side member 213 and the support member 330. According to another embodiment, the resonance space 230 may be defined as a space provided by the through hole 240 and a space disposed between at least a portion of the inner surface 213a of the side member 213 and the support member 330.

According to various embodiments, the inner surface 213a of the side member 213 may have various shapes. According to an embodiment, the inner surface 213a of the side member 213 may include a first inner surface I1 which is in contact with the adhesive sheet 350, a second inner surface I2 which is substantially perpendicular to the adhesive sheet 350, and a third inner surface I3 which faces the adhesive sheet 350 and is spaced apart from the adhesive sheet 350. The third inner surface I3 may extend from the second inner surface I2 to the through hole 240. For example, the resonance space 230 may be defined by the first inner surface I1, the second inner surface I2, the third inner surface I3, the fourth inner surface I4, and the through hole.

According to various embodiments, the resonance space 230 may be configured in a structure that facilitates discharging foreign substances introduced into the resonance space 230 through the through hole 240. For example, the fourth inner surface I4 of the through hole 240 or the resonance space 230 may be configured to be flat in the third direction (the +Y direction) to prevent foreign substances from remaining. Foreign substances introduced into the resonance space 230 through the through hole 240 can be easily discharged by a sound pressure generated according to the operation of the speaker assembly 320.

According to various embodiments, the fixing member 340 may couple the speaker assembly 320 to the support member 330. The fixing member 340 may be provided by processing, for example, a plate including a metal. The fixing member 340 will be described in detail with reference to FIG. 7.

According to various embodiments, the adhesive sheet 350 may be disposed between the support member 330 and the side member 213. According to an embodiment, the adhesive sheet 350 may include an adhesive material to couple the support member 330 to the side member 213. According to another embodiment, the adhesive sheet 350 may be configured to block the introduction of moisture and foreign substances from the outside into the space between the support member 330 and the inner surface 213a of the side member 213. For example, the adhesive sheet 350 may be a double-sided tape having a waterproof function.

According to various embodiments, the battery 370 may supply power to at least one component of the electronic device 200. The battery 370 may include, for example, a non-rechargeable primary cell, a rechargeable secondary cell, or a fuel cell. The battery 370 may be disposed inside the housing (e.g., the housing 210 in FIG. 2A). For example, the battery 370 may be disposed between the display 400 and the first circuit board 310. The battery may be integrally disposed inside the electronic device 200, or may be disposed to be detachable/attachable from/to the electronic device 200.

According to various embodiments, the display 400 may be disposed on the inner surface of the window member 211 and may be exposed through the window member 211. The display 400 may have a shape corresponding to the shape of the window member 211. For example, the display 400 may have a circular shape, an oval shape, or a polygonal shape. The display 400 may include a first bent unit 414 configured to electrically connect a touch sensor (e.g., the touch sensor 412 in FIG. 9) to a second circuit board (e.g., the second circuit board 430 in FIG. 9). In an embodiment, the first bent unit 414 may be disposed in the third direction (the +Y direction) in which the through hole 240 is provided. The display 400 will be described in more detail with reference to FIG. 9.

Figure 6A:
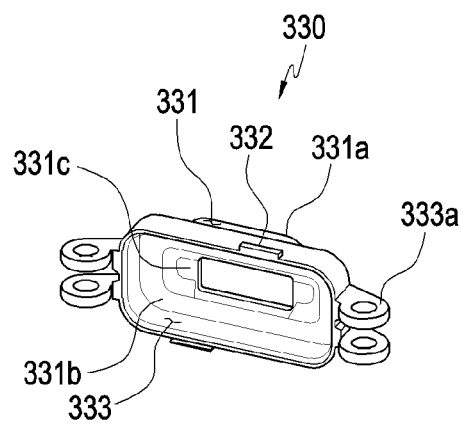
FIG. 6A illustrates a perspective view of a support member of an electronic device according to various embodiments of the disclosure.
Figure 6B:
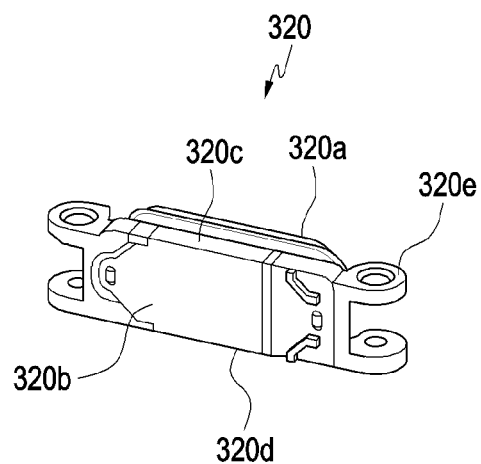
FIG. 6B illustrates a perspective view of a speaker assembly of the electronic device according to various embodiments of the disclosure.

FIG. 6A illustrates a perspective view of a support member of an electronic device according to various embodiments of the disclosure, and FIG. 6B illustrates a perspective view of a speaker assembly of the electronic device according to various embodiments of the disclosure. All or a part of the configurations of the support member 330 of FIG. 6A and the speaker assembly 320 of FIG. 6B may be the same as those of the support member 330 and the speaker assembly 320 of FIG. 5.

According to FIG. 6A, the support member 330 may include a first portion 331 on which a third surface 331a facing at least a portion of the inner surface 213a of the side member 213 and a fourth surface 331b facing away from the third surface 331a are disposed, and a second portion 333 extending from the first portion 331 and surrounding the speaker assembly 320.

According to various embodiments, the support member 330 may be disposed in various directions in the electronic device (e.g., the electronic device 200 in FIG. 2A). For example, the third surface 331a may be provided to be perpendicular to the third direction (e.g., the third direction (the +Y direction) in FIG. 5) in which the through hole 240 is disposed, and the fourth surface 331b may be provided to face away from the third surface 331a (e.g., the +Y direction in FIG. 5).

According to various embodiments, the first portion 331 may be provided in a closed loop shape. According to an embodiment, the third surface 331a of the first portion 331 may be coupled to at least a portion of the inner surface 213a of the side member 213 via the adhesive sheet 350. According to another embodiment, the fourth surface 331b of the first portion 331 may be in contact with the speaker assembly 320.

According to various embodiments, the fourth surface 331b may have a shape corresponding to the shape of the speaker assembly 320. According to an embodiment, a recess 331c providing a space in which at least a portion of the first surface 320a of the speaker assembly 320 is accommodated may be disposed in the fourth surface 331b. According to another embodiment, the fourth surface 331b may be provided as a flat surface.

According to various embodiments, the second portion 333 may extend from the first portion 331 so as to surround at least a portion of the speaker assembly 320. For example, the second portion 333 may extend in a perpendicular direction from the first portion 331 to provide a space in which at least a portion of the speaker assembly 320 is seated.

According to various embodiments, the support member 330 may include at least one second fastening hole 333a. The second fastening hole 333a may be provided to extend from the second portion 333. The support member 330 may be coupled to the speaker assembly 320 or the side member (e.g., the side member 213 in FIG. 5) through the second fastening hole 333a.

According to various embodiments, the support member 330 may include at least one support protrusion 332. The support protrusion 332 may extend from the outer surface of the second portion 333 to be coupled with a fixing member (e.g., the fixing member 340 in FIG. 5).

According to FIG. 6B, the speaker assembly 320 may include a first surface 320a on which the speaker diaphragm (not illustrated) facing the through hole (e.g., the through hole 240 in FIG. 5) or the resonance space (e.g., the resonance space 230 in FIG. 5) is disposed, and a second surface 320b facing away from the first surface 320a.

According to various embodiments, the speaker assembly 320 may include a first surface 320a, a second surface 320b, and an outer surface surrounding the space between the first surface 320a and the second surface 320b. For brevity of description, a portion of the outer surface is defined as a fifth surface 320c, and a portion of the outer surface that is disposed opposite to the fifth surface 320c and is perpendicular to the first surface 320a or the second surface 320b is defined as a sixth surface 320d. When the speaker assembly 320 is mounted on the support member 330, according to an embodiment, the first surface 320a may face the fourth surface 331b of the support member 330, and the fifth surface 320c and the sixth surface 320d may be in contact with the inner surface of the second portion 333. The area of the fourth surface 331b facing the first surface 320a may be greater than the area of the recess 331c in which the first surface 320a is accommodated. According to various embodiments, a speaker diaphragm (not illustrated) may be disposed on the first surface 320a. The first surface 320a may be substantially defined as a sound output surface of the speaker assembly 320. The speaker diaphragm may be disposed in a direction perpendicular to the third direction (e.g., the +Y direction in FIG. 5) oriented toward the through hole (e.g., the through hole 240 in FIG. 5) so that the sound generated by the speaker diaphragm can be output to the outside.

According to various embodiments, the speaker assembly 320 may include at least one first fastening hole 320e. The first fastening hole 320e may extend from an outer surface of the speaker assembly 320. The speaker assembly 320 may be coupled to the support member 330 and/or the side member (e.g., the side member 213 of FIG. 5) through the first fastening hole 320e.

Figure 7:
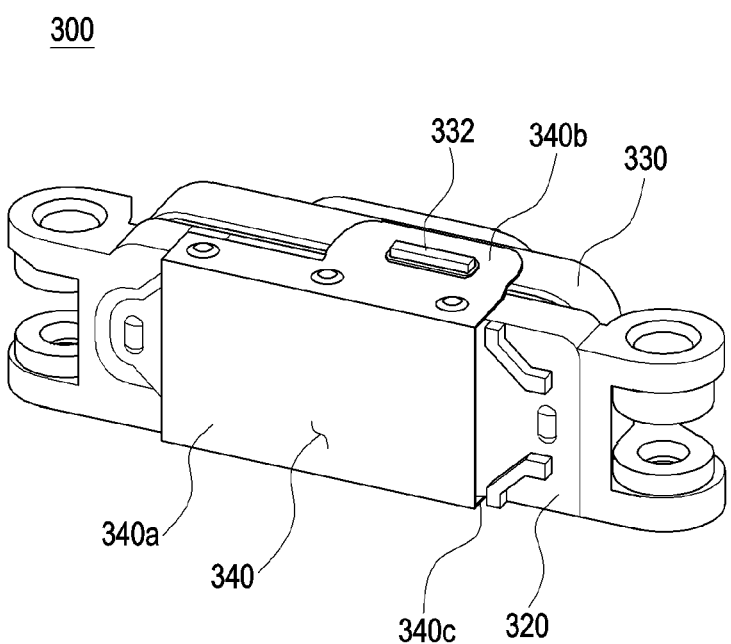
FIG. 7 illustrates a perspective view of a speaker device according to various embodiments of the disclosure.

FIG. 7 illustrates a perspective view of a speaker device according to various embodiments of the disclosure.

Referring to FIG. 7, the speaker device 300 may include a speaker assembly 320, a support member 330, and/or a fixing member 340. All or a part of the configurations of the speaker assembly 320, the support member 330, and the fixing member 340 of FIG. 7 may be the same as those of the speaker assembly 320, the support member 330, and the fixing member 340 of FIGS. 5, 6A and 6B.

According to various embodiments, the fixing member 340 may be formed to press at least a portion of the speaker assembly 320 and at least a portion of the support member 330. For example, the fixing member 340 may include a third portion 340a which is in contact with at least a portion of the second surface of the speaker assembly 320 (e.g., the second surface 320b of FIG. 6B), a fourth portion 340b which is in contact with the fifth surface (e.g., the fifth surface 320c in FIG. 6B) of the speaker assembly 320, and a fifth portion 340c which is in contact with the sixth surface (e.g., the sixth surface 320d in FIG. 6B) of the speaker assembly 320.

According to various embodiments, the fixing member 340 may couple the speaker assembly 320 to the support member 330. The fixing member 340 may have a structure surrounding at least a portion of the speaker assembly 320 and the support member 330 and may be coupled to the support member 330 to prevent the speaker assembly 320 from being separated from the support member 330. According to an embodiment, the fixing member 340 may be coupled to the support member 330 via the fourth portion 340b having an opening configured to correspond to the support protrusion 332. According to another embodiment, the fixing member 340 may be coupled to the support member 330 via the fifth portion 340c having an opening configured to correspond to the support protrusion 332. According to another embodiment, the fixing member 340 may be coupled to the outer surface of the support member 330 via the fourth portion 340b having an opening configured to correspond to the support protrusion 332 and the fifth portion 340c having an opening configured to correspond to the support protrusion 332.

Figure 8A:
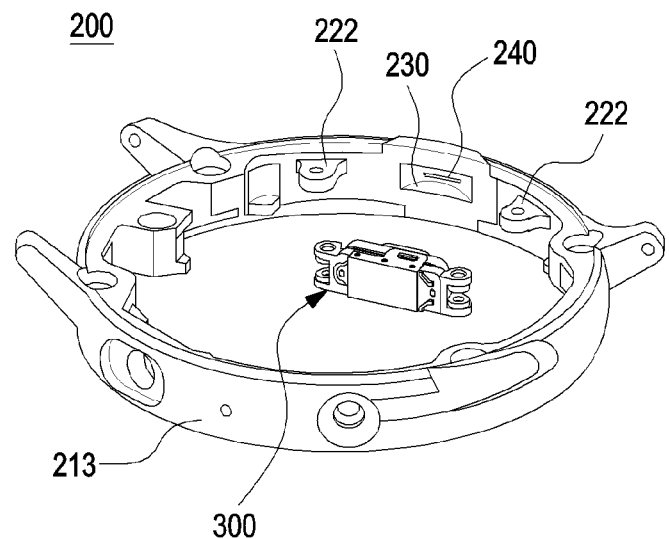
FIG. 8A illustrates a view illustrating a speaker device coupled to a side member, according to various embodiments of the disclosure.
Figure 8B:
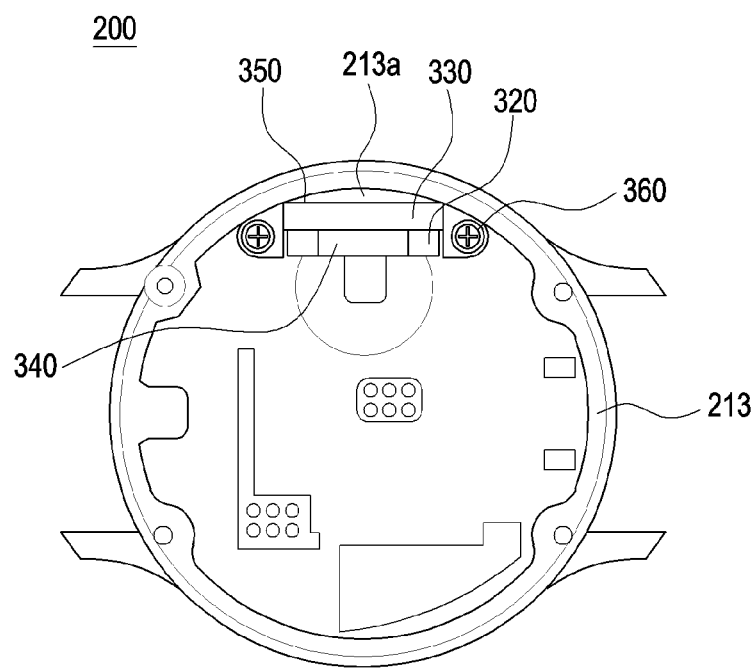
FIG. 8B illustrates a front view of an electronic device in which the speaker device is coupled to the side member, according to various embodiments of the disclosure.

FIG. 8A illustrates a view illustrating a speaker device coupled to a side member, according to various embodiments of the disclosure, and FIG. 8B illustrates a front view of an electronic device in which the speaker device is coupled to the side member, according to various embodiments of the disclosure.

According to FIGS. 8A and 8B, the electronic device 200 may include a side member 213 and a speaker device 300. All or a part of the configuration of the speaker device 300 of FIGS. 8A and 8B may be the same as that of the speaker device 300 of FIG. 7, and all or a part of the configuration of the side member 213 of FIGS. 8A and 8B may be the same as that of the side member 213 of FIG. 5.

According to FIGS. 8A and 8B, the speaker device 300 may be coupled to the inner surface 213a of the side member 213 via the fastening member 360. For example, the fastening member 360 may be inserted into the first fastening hole 320e and the second fastening hole 333a through the fastening groove 222 in the side member 213. The speaker assembly 320 and the support member 330 may be coupled to the side member 213 by the fastening member 360 inserted into the first fastening hole 320e and the second fastening hole 333a.

According to various embodiments, the volume of the internal space required for disposition of the speaker device 300 in the electronic device 200 may be reduced. For example, since the speaker device 300 is coupled to the side member 213 rather than to the rear housing (e.g., the rear housing 215 of FIG. 3), the rear housing (e.g., the rear housing 215 of FIG. 3) may not be provided with a recess for seating the speaker assembly (e.g., the speaker assembly 320 in FIG. 7). According to an embodiment, the speaker assembly 320 may be disposed in the resonance space 230 provided in a recess shape in the side member 213. For example, the speaker diaphragm (not illustrated) of the speaker assembly 320 may be disposed to face at least a portion of the resonance space 230. In the electronic device 200 in which the speaker assembly 320 is disposed in the resonance space 230, the thickness of the rear housing 215 for providing the recess is not increased, and the thickness of the side member 213 is not increased as well due to the provision of the resonance space 230. Therefore, the speaker assembly 320 can be reduced in the thickness compared to that in an electronic device in which the speaker assembly 320 is disposed in the recess provided in the rear housing 215, and the size of a space allowable for another electronic component, for example, a battery (e.g., the battery 370 in FIG. 5) can be increased.

Figure 9:
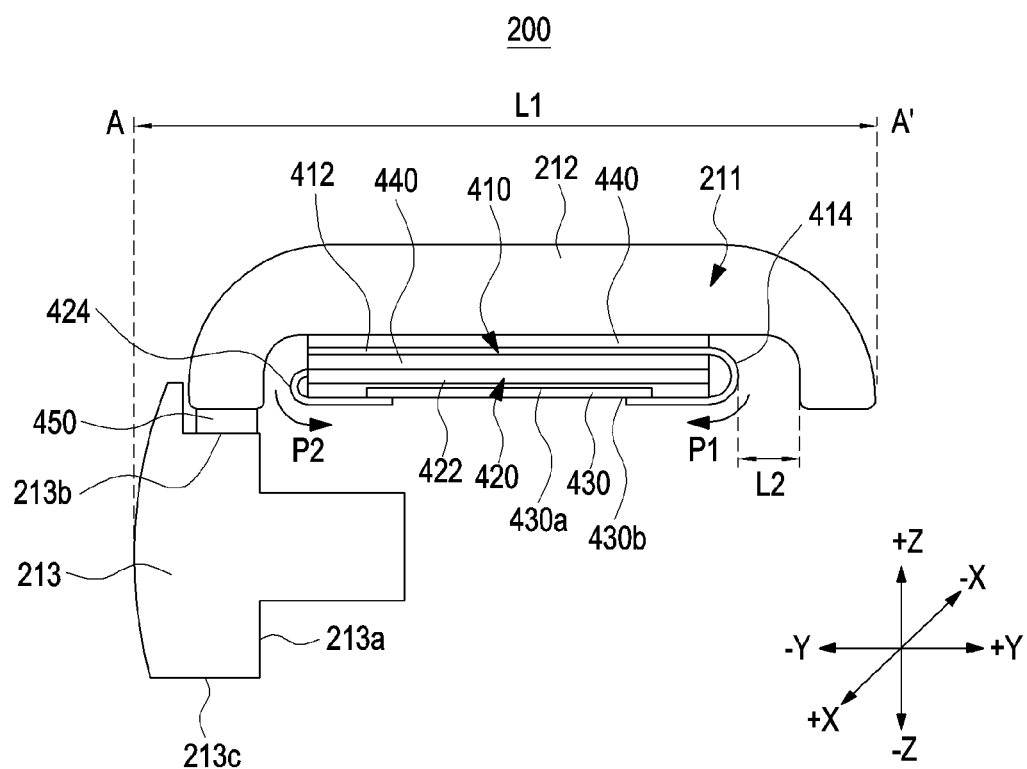
FIG. 9 illustrates a cross-sectional view of an electronic device according to various embodiments of the disclosure.

FIG. 9 illustrates a cross-sectional view of an electronic device according to various embodiments of the disclosure.

In FIG. 9, the "+Z" direction may indicate a first direction, and the "−Z" direction may indicate a second direction.

Referring to FIG. 9, an electronic device 200 may include a window member 211, a first plate 212, a side member 213, and/or a display 400.

All or a part of the configurations of the window member 211, the side member 213, and the display 400 of FIG. 9 may be the same as those of the window member 211, the side member 213, and the display 400 of FIG. 5.

According to various embodiments, the display 400 has a configuration corresponding to a display device (e.g., the display device 160 in FIG. 1) and may include a touch sensor module 410, a display module 420, and a second circuit board 430, and/or an adhesion film 440.

According to various embodiments, the window member 211 may be coupled to the top surface 213b of the side member 213 via a sealing member 450 including an adhesive material. For example, the sealing member 450 may be configured to block moisture or foreign substances introduced from the outside into the space between the window member 211 and the side member 213.

According to various embodiments, the window member 211 may include a first plate 212. The first plate 212 is defined as an area of at least a portion of the window member 211 provided in a direction perpendicular to the first direction (the +Z direction). The first plate 212 may be disposed in the electronic device 200 to be substantially parallel to the top surface 213b of the side member 213. The first plate 212 may be made of a transparent material such as glass or resin (e.g., acrylic or polycarbonate) to provide a user with a screen output from the display device (e.g., the display device 160 of FIG. 1).

According to various embodiments, the touch sensor module 410 may include a touch sensor 412 and a first bent unit 414. According to an embodiment, in the touch sensor module 410, the touch sensor 412 and the first bent unit 414 may be integrated with each other. According to another embodiment, the touch sensor module 410 may be provided by coupling the first bent unit 414 made of a flexible circuit board to the touch sensor 412.

According to various embodiments, the touch sensor 412 may be included in a display device (e.g., the display device 160 in FIG. 1). The touch sensor 412 may include a plurality of patterns to receive a user's input. For example, the touch sensor 412 may include a touch detection circuit configured to detect a touch or a sensor circuit (e.g., a pressure sensor) configured to measure the intensity of a force generated by the touch.

According to various embodiments, the touch sensor 412 may be disposed under the first plate 212 (e.g., in the −Z direction). For example, the touch sensor 412 may be disposed in the second direction (the −Z direction) with respect to the first plate 212 via the adhesion film 440. For example, the adhesion film 440 may be an optically clear and adhesion film.

According to various embodiments, the first bent unit 414 may provide a signal path through which the touch sensor 412 is electrically connected to the second circuit board 430. According to an embodiment, the first bent unit 414 may extend from the touch sensor 412 to the second circuit board 430 in the first bending direction (the direction P1). For example, as illustrated in FIG. 9, the first bending direction (the direction P1) may refer to a direction extending from the +Z axis, passing through the +Y axis, and bent to the −Z axis on the YZ plane, as illustrated in FIG. 9.

According to various embodiments, the display module 420 may be formed of an unbreakable (UB) panel made of a flexible plastic material, and may include a display panel 422 configured to visually provide information to the outside of the electronic device 200 and a second bent unit 424 electrically connecting the display panel 422 to the second circuit board 430.

According to various embodiments, the display panel 422 may be disposed between the touch sensor 412 and the second circuit board 430. For example, the display panel 422 may be disposed in the second direction (the −Z direction) with respect to the touch sensor 412 via the adhesion film 440.

According to various embodiments, the second bent unit 424 may provide a signal path through which the display panel 422 is electrically connected to the second circuit board 430. For example, the second bent unit 424 may extend from the display panel 422 to the second circuit board 430 in the second bending direction (the direction P2). The second bending direction (the direction P2) may be formed in a direction different from the first bending direction (the direction P1). According to an embodiment, as illustrated in FIG. 9, the second bending direction (the direction P2) may refer to a direction extending from the +Z axis, passing through the −Y axis, and then extending to the −Z axis on the YZ plane. According to another embodiment, the second bending direction (the direction P2) may refer to a direction extending from the +Z axis, passing through the −X axis, and bent to the −Z axis on the ZX plane.

According to various embodiments, since the second bending direction (the direction P2) is different from the first bending direction (the direction P1), the ratio of a second length L2 to a first length L1 of the electronic device 200 can be reduced. The first length L1 may be defined as the length of the diameter of the electronic device 200 on the XY plane. The second length L2 may be defined as a distance from the first bent unit 414 or the second bent unit 424 to the side member 213 on the XY plane. When the ratio of the second length L2 to the first length L1 is reduced, the ratio of the area on which the electronic device 200 displays a screen can be increased.

According to various embodiments, the second circuit board 430 may obtain an input to the touch sensor 412. For example, the second circuit board 430 may receive information about an input to the touch sensor 412 via the first bent unit 414.

According to various embodiments, the second circuit board 430 may provide an electrical signal path for a processor (e.g., the processor 120 in FIG. 1) to control the operation of at least one of the touch sensor 412 or the display module 420. For example, the processor 120 may transmit, to the touch sensor 412, a command or an instruction configured to control the operation of the touch sensor 412, via the first bent unit 414 included in the second circuit board 430. As another example, the processor 120 may transmit, to the display panel 422, a command or an instruction configured to control the operation of the display panel 422, via the second bent unit 424 included in the second circuit board 430.

According to various embodiments, the second circuit board 430 may be disposed in the second direction (the −Z direction) with respect to the first plate 212. According to an embodiment, the second circuit board 430 may be disposed under the display panel 422. According to another embodiment, the second circuit board 430 may be integrated with the display panel 422 under the display panel 422.

According to various embodiments, the second circuit board 430 may include a top surface 430a configured to be coupled to the display panel 422, and a bottom surface 430b configured to be coupled to the first bent unit 414 and the second bent unit 424. According to an embodiment, the second circuit board 430 may be physically connected to the display panel 422 via the top surface 430a, may be electrically connected to the touch sensor 412 via the first bent unit disposed on the bottom surface 430b, and may be electrically connected to the display panel 422 via the second bent unit 424 disposed on the bottom surface 430b. According to another embodiment, the second circuit board 430 may be physically and electrically connected to the display panel 422 via the top surface 430a.

According to an embodiment, the second bent unit 424 may be provided to extend from substantially the same plane as the second circuit board 430. For example, a recess for accommodating the second circuit board 430 may be provided in the display module 420, and the second bent unit 424 may be provided to extend from a side surface of the display module 420 provided on substantially the same plane as the second circuit board 430.

Figure 10A:
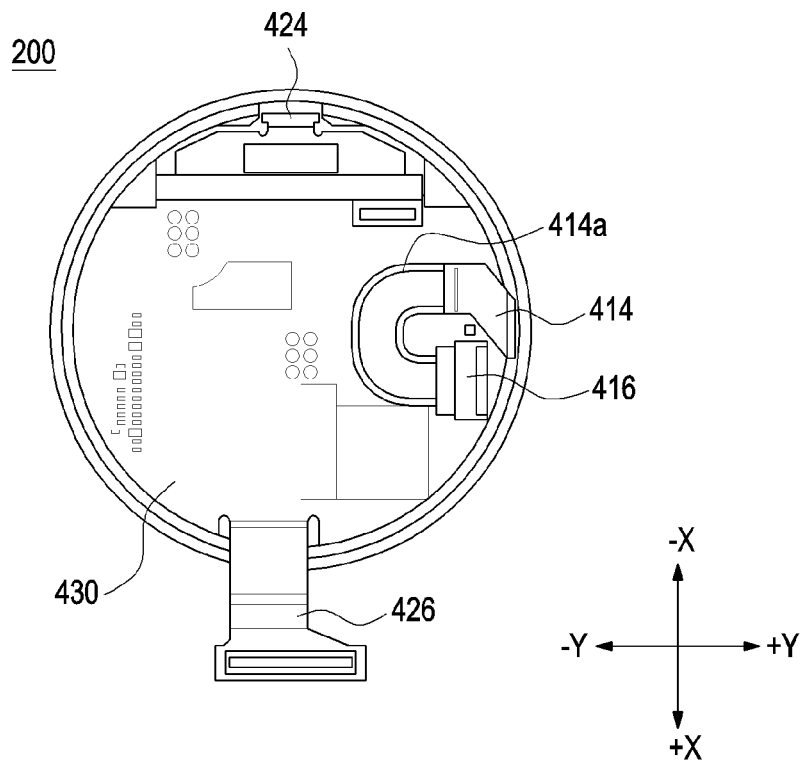
FIG. 10A illustrates a display module and a second circuit board according to various embodiments of the disclosure.
Figure 10B:
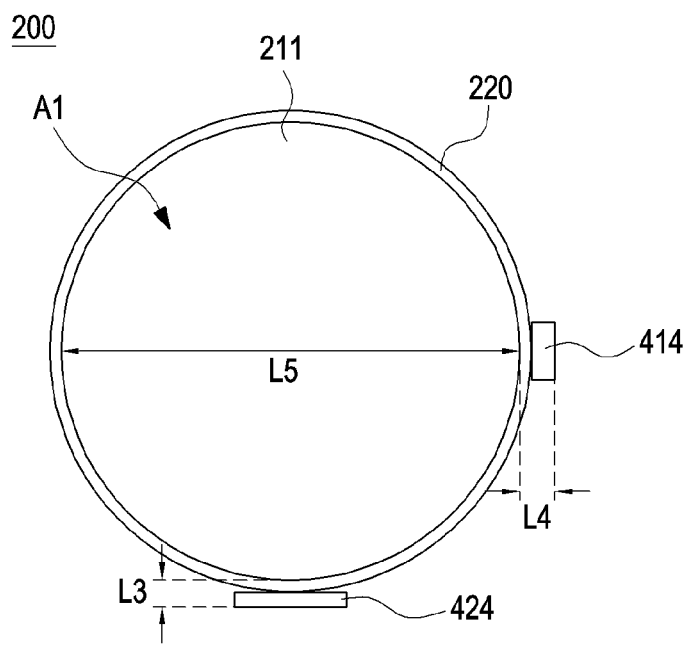
FIG. 10B illustrates a bezel of an electronic device according to various embodiments of the disclosure.

FIG. 10A illustrates a view illustrating a display module and a second circuit board according to various embodiments of the disclosure, and FIG. 10B illustrates a view illustrating a bezel of an electronic device according to various embodiments of the disclosure.

According to FIGS. 10A and 10B, the electronic device 200 may include a first bent unit 414, a connector 416, a second bent unit 424, a third bent unit 426, and/or a second circuit board 430. All or a part of the configurations of the first bent unit 414, the second bent unit 424, and the second circuit board 430 of FIG. 10A may be the same as those of the first bent unit 414, the second bent unit 424, and the second circuit board 430 of FIG. 9.

According to various embodiments, the first bent unit 414 may be coupled to the second circuit board 430 via the connector 416. According to an embodiment, the connector 416 may include a zigzag in-line package (ZIP) connector. The connector 416 may be disposed on the bottom surface (e.g., the bottom surface 430b in FIG. 9) of the second circuit board 430.

According to various embodiments, the first bent unit 414 may have a curved shape for easy connection with the connector 416. For example, the first bent unit 414 may be bent in a "U" shape. As the first bent unit 414 has a curved shape, the length L4 of the first bent unit on which the first bent unit 414 is disposed can be reduced, and thus the size of the bezel 220 can be reduced.

According to various embodiments, the second circuit board 430 may include a groove 414a corresponding to the first bent unit 414. Since the first bent unit 414 is seated in the groove 414a, the thickness of the inside of the electronic device 200 formed by the first bent unit 414 can be reduced. The groove 414a may be provided in the bottom surface 430b of the second circuit board 430.

According to various embodiments, the size of the area A1 that is capable of substantially providing visual information in the electronic device 200 may be determined based on the first bent unit 414 or the second bent unit 424. For example, the size of the area A1 that is capable of substantially providing visual information in the electronic device 200 may be determined based on a fourth length L4 that is a length of the first bent unit 414 exposed from the touch sensor (e.g., the touch sensor 412 in FIG. 9) when the electronic device 200 is viewed in a direction perpendicular to the top surface (e.g., 430a of FIG. 9) of the second circuit board 430 or a third length L3 that is a length of the second bent unit 424 exposed from the display panel (e.g., the display panel 422 of FIG. 9) when the electronic device 200 is viewed in the direction perpendicular to the top surface of the second circuit board 430. For convenience of description, the area A1 that is capable of substantially providing visual information in the electronic device 200 is defined as a visible area.

According to various embodiments, the first bent unit 414 and the second bent unit 424 may be disposed in directions that are substantially perpendicular to each other. For example, a direction in which an end of the first bent unit 414 connected to the connector 416 is oriented may be perpendicular to a direction in which an end of the second bent unit 424 connected to the second circuit board 430 is oriented. As another example, a direction in which an end of the first bent unit 414 connected to the touch sensor 412 is oriented may be perpendicular to a direction in which an end of the second bent unit 424 connected to the display panel 422 is oriented.

According to various embodiments, the size of the visible area A1 may be determined based on at least one of the third length L3 and the fourth length L4. For example, the size of the visible area A1 may be determined based on the longer length from among the third length L3 or the fourth length L4.

According to various embodiments, when the first bent unit 414 and the second bent unit 424 are disposed in different directions, the third length L3 or the fourth length L4 may be reduced compared to that in the case in which the first bent unit 414 and the second bent unit 424 are disposed in the same direction. According to an embodiment, the size of the visible area A1 in the electronic device 200 in which the first bent unit 414 and the second bent unit 424 are disposed in directions that are substantially perpendicular to each other may be greater than the size of the visible area in the electronic device 200 in which the first bent unit 414 and the second bent unit 424 are disposed in substantially the same direction. For example, when a fifth length L5 that is the length of the diameter of the visible area A1 is about 42 mm, and when the first bent unit 414 and the second bent unit 424 are disposed in directions that are substantially perpendicular to each other, the third length L3 may be 2.207 mm, and the fourth length L4 may be 2.204 mm. In the case in which the first bent unit 414 and the second bent unit 424 are disposed in substantially the same direction, the exposed length of the first bent unit 414 and the second bent unit 424 when the electronic device 200 corresponding to the third length L3 or the fourth length L4 is viewed from above may be 4.84 mm. According to another embodiment, the size of the bezel of the electronic device 200 in which the first bent unit 414 and the second bent unit 424 are disposed in different directions may be smaller than the size of the bezel in the case in which the first bent unit 414 and the second bent unit 424 are disposed in different directions.

According to various embodiments, the third bent unit 426 may be provided to extend from the second circuit board 430. The third bent unit 426 may be configured to electrically connect the second circuit board 430 and the first circuit board that controls the operation of the electronic device 200 (e.g., the first circuit board 310 in FIG. 5) to each other. According to an embodiment, the third bent unit 426 may be disposed in a direction (the +X direction) opposite to the direction (the −X direction) in which the second bent unit 424 is disposed on the second circuit board 430. According to another embodiment, the third bent unit 426 may be disposed on the second circuit board 430 in a fifth direction (the +X direction) that is opposite to the fourth direction (the −X direction) in which the second bent unit is disposed and is substantially perpendicular to the third direction (the +Y direction) in which the first bent unit 414 is disposed.

According to various embodiments of the present disclosure, an electronic device (e.g., the electronic device 200 in FIG. 2A) may include a window member (e.g., the window member 211 in FIG. 9) oriented in a first direction (e.g., the first direction (+Z direction) in FIG. 9), a rear housing (e.g., the rear housing 215 in FIG. 3) oriented in a second direction (e.g., the second direction (−Z direction) in FIG. 9) opposite to the first direction, a housing (e.g., the housing 210 in FIG. 2A) including a side member (e.g., the side member 213 in FIG. 3) surrounding a space between the window member and the rear housing, a display (e.g., the display 400 in FIG. 5) visible through at least a portion of the window member, and a speaker assembly disposed in the space and including a speaker diaphragm (e.g., the speaker assembly 320 in FIG. 6B), wherein the side member may include a resonance space (e.g., the resonance space 230 in FIG. 5) shaped in the form of a recess in a third direction (e.g., the third direction (+Y direction) in FIG. 5) substantially perpendicular to the first direction or the second direction from the space, and at least one through hole (e.g., the through hole 240 in FIG. 5) provided in the third direction in a portion of the resonance space closer to the rear housing than the window member, wherein at least a portion of the resonance space may be disposed to overlap the speaker diaphragm when the resonance space is viewed in the third direction.

According to various embodiments, the electronic device may further include a support member (e.g., the support member 330 in FIG. 6A) coupled to the side member and provided to surround at least a portion of the speaker assembly.

According to various embodiments, the speaker assembly may include a first surface (e.g., the first surface 320a in FIG. 6B) facing at least a portion of an inner surface of the side member and a second surface (e.g., the second surface 320b in FIG. 6B) facing away from the first surface.

The support member may include a first portion (e.g., the first portion 331 in FIG. 6A) including a third surface (e.g., the third surface 331a in FIG. 6A) facing at least a portion of the inner surface of the side member and a fourth surface (e.g., the fourth surface 331b in FIG. 6A) facing at least a portion of the first surface, and a second portion (e.g., the second portion 333 in FIG. 6A) extending from the first portion and surrounding the speaker assembly.

According to various embodiments, the electronic device may further include a fixing member (e.g., the fixing member 340 in FIG. 7) disposed on the speaker assembly and the support member in order to press at least a portion of the speaker assembly and the support member.

According to various embodiments, the side member may include a first inner surface (e.g., the first inner surface I1 in FIG. 5) facing the support member, a second inner surface (e.g., the second inner surface I2 in FIG. 5) substantially perpendicular to the first inner surface, a third inner surface I3 extending from the second inner surface to the through hole, and a fourth inner surface facing the second inner surface.

According to various embodiments, the display may include a second circuit board (e.g., the second circuit board 430 of FIG. 9) disposed in a second direction with respect to the window member, a touch sensor module (e.g., the touch sensor module 410 of FIG. 9) including a touch sensor (e.g., the touch sensor 412 in FIG. 9) disposed between the window member and the second circuit board and a first bent unit (e.g., the first bent unit 414 in FIG. 9) extending from the touch sensor in the third direction and configured to electrically connect the touch sensor and the second circuit board to each other, and a display module (e.g., the display module 420 in FIG. 9) including a display panel (e.g., the display panel in FIG. 9)(e.g., the display panel 422 in FIG. 9) disposed between the touch sensor and the second circuit board, and a second bent unit (e.g., the second bent unit 424 in FIG. 9) extending in a fourth direction (e.g., the fourth direction (the −Y direction) in FIG. 9) which is a direction different from the third direction and configured to electrically connect the display panel and the second circuit board to each other.

According to various embodiments, the first bent unit may at least partially overlap the speaker assembly when the display is viewed in the first direction.

According to various embodiments, the electronic device may further include a first circuit board (e.g., the first circuit board 310 in FIG. 3) on which a processor configured to control the operation of the electronic device is mounted, and the second circuit board may include a third bent unit extending from the second circuit board in a fifth direction (e.g., the fifth direction (+X direction) in FIG. 10A) opposite to the fourth direction and configured to electrically connect the first circuit board and the second circuit board to each other.

According to various embodiments, the third direction and the third direction may be perpendicular to each other.

According to various embodiments of the disclosure, an electronic device (e.g., the electronic device 200 in FIG. 2A) may include a side member (e.g., the inner surface 213a of the side member in FIG. 3) including a through hole (e.g., the through hole 240 in FIG. 3) provided therethrough, a rear housing (e.g., the rear housing 215 in FIG. 2B) coupled to the side member, a speaker assembly (e.g., the speaker assembly 320 in FIG. 6B) including a first surface (e.g., the first surface 320a in FIG. 6B) on which a speaker diaphragm facing the through hole is disposed and a second surface (e.g., the second surface 320b in FIG. 6B) facing away from the first surface, a support member (e.g., the support member 330 in FIG. 6A) coupled to the side member and provided to surround at least a portion of the speaker assembly, and a fixing member (e.g., the fixing member 340 in FIG. 7) configured to press at least a portion of the speaker assembly and the support member, wherein a resonance space (e.g., the resonance space 230 in FIG. 5) may be provided between at least a portion of the inner surface of the side member (e.g., the inner surface 213a of the side member in FIG. 3) and the support member.

According to various embodiments, the support member may include a first portion (e.g., the first portion 331 in FIG. 6A) in which a third surface (e.g., the third surface 331a in FIG. 6A) facing at least a portion of the inner surface of the side member and a fourth surface (e.g., the fourth surface 331b in FIG. 6A) facing away from the third surface are disposed, and a second portion (e.g., the second portion 333 in FIG. 6A) extending from the first portion and surrounding the speaker assembly.

According to various embodiments, the speaker assembly may include a fifth surface (e.g., the fifth surface 320c in FIG. 6B) perpendicular to the first surface or the second surface, and a sixth surface (e.g., the sixth surface 320d of FIG. 6B) perpendicular to the first surface or the second surface and disposed in a direction opposite to the fifth surface, and the fixing member may include a third portion (e.g., the third portion 340a in FIG. 7) which is in contact with at least a portion of the second surface, a fourth portion (e.g., the fourth portion 340b in FIG. 7) which is in contact with at least a portion of the fifth surface, and a fifth portion (e.g., the fifth portion 340c in FIG. 7) which is in contact with at least a portion of the sixth surface.

According to various embodiments, the support member may include a support protrusion (e.g., the support protrusion 332 in FIG. 7) provided on the second portion, and the fixing member may be provided on at least one of the fourth portion or the fifth portion and may include an opening configured to correspond to the support protrusion.

According to various embodiments, the electronic device may further include an adhesive sheet (e.g., the adhesive sheet 350 in FIG. 5) disposed between the inner surface of the side member and the third surface and configured to couple the support member to the side member.

According to various embodiments, the electronic device may further include a fastening member (e.g., the fastening member 360 in FIG. 8B) configured to couple the speaker assembly and the support member to the side member.

According to various embodiments, the speaker assembly may include a first fastening hole (e.g., the first fastening hole 330e in FIG. 6B) provided to extend from the speaker assembly, the support member may include a second fastening hole (e.g., the second fastening hole 333a in FIG. 6A) provided to extend from the second portion, wherein the speaker assembly and the support member may be coupled to the side member by the fastening member inserted into the first fastening hole and the second fastening hole.

According to various embodiments, the through hole may be provided to extend from the resonance space.

According to various embodiments of the disclosure, an electronic device may include a window member (e.g., the window member 211 in FIG. 5) at least a portion of which is substantially transparent, a second circuit board (e.g., the second circuit board 430 in FIG. 9), a touch sensor module (e.g., the touch sensor module in FIG. 9) including a touch sensor (e.g., the touch sensor 412 in FIG. 9) disposed under the window member and a first bent unit (e.g., the first bent unit 414 in FIG. 9) extending from the touch sensor in a first bending direction (the first bending direction (the direction P1) in FIG. 9) and configured to electrically connect the touch sensor and the second circuit board, and a display module (e.g., the display module 420 in FIG. 9) including a display panel (e.g., the display panel 422 in FIG. 9) disposed between the touch sensor and the second circuit board, and a second bent unit (e.g., the second bent unit 424 in FIG. 9) extending from the display panel in a second bending direction (e.g., the second bending direction (the direction P2) in FIG. 9) different from the first bending direction and configured to electrically connect the display panel and the first circuit board to each other.

According to various embodiments, the second circuit board may include a top surface (e.g., the top surface 430a in FIG. 9) coupled to the display panel, and a bottom surface (e.g., the bottom surface 430b in FIG. 9) coupled to the first bent unit and the second bent unit.

According to various embodiments, the first bent unit has a "U" shape, and a groove (e.g., the groove 414a in FIG. 10A) corresponding to the first bent unit may be provided in the bottom surface.

According to various embodiments, the electronic device may further include a first circuit board (e.g., the first circuit board 310 in FIG. 5) configured to control the operation of the wearable electronic device, wherein the first circuit board may include a third bent unit (e.g., the third bent unit 426 in FIG. 10A) extending from the first circuit board in a third bending direction opposite to the second bending direction and configured to electrically connect the first circuit board and the second circuit board to each other.

According to various embodiments, the display panel may be made of an unbreakable (UB) panel.

According to various embodiments of the disclosure, a wearable electronic device may include a side member including a top surface (e.g., the top surface 213b in FIG. 9) oriented in a first direction (e.g., the first direction (the +Z direction) in FIG. 9) and a bottom surface (e.g., the bottom surface 213c in FIG. 9) oriented in a second direction (e.g., the second direction (the -Z direction) in FIG. 9) opposite to the first direction, wherein the side member includes a through hole provided therethrough in a third direction (e.g., the third direction (the +Y direction) in FIG. 5) which is substantially perpendicular to the first direction or the second direction, a speaker assembly including a speaker diaphragm oriented in the third direction, a support member coupled to an inner surface of the side member and provided to surround at least a portion of the speaker assembly, a first plate extending from the first surface and oriented in the first direction, a first circuit board disposed in the second direction with respect to the first plate, a touch sensor module including a touch sensor disposed in the second direction with respect to the first plate, and a first bent unit extending from the touch sensor in the third direction and configured to electrically connect the touch sensor and the first circuit board to each other, and a display module including a display panel disposed in the second direction with respect to the touch sensor and a second bent unit extending from the display panel in a fourth direction (e.g., the fourth direction (-Y direction) in FIG. 5) which is different from the third direction and configured to electrically connect the display panel and the second circuit board to each other.

It may be apparent to a person ordinarily skilled in the technical field to which the disclosure belongs that an electronic device including a speaker assembly according to various embodiments of the disclosure is not limited by the above-described embodiments and drawings, and can be variously substituted, modified, and changed within the technical scope of the disclosure.

Although the present disclosure has been described with various embodiments, various changes and modifications may be suggested to one skilled in the art. It is intended that the present disclosure encompass such changes and modifications as fall within the scope of the appended claims.

What is claimed is:

1. An electronic device comprising:
a housing including a window member oriented in a first direction, a rear housing oriented in a second direction that is opposite to the first direction, and a side member surrounding a space between the window member and the rear housing;
a display that is visible through at least a portion of the window member; and
a speaker assembly disposed in the space and including a speaker diaphragm,
wherein the side member includes:
a resonance space having a shape recessed from the space in a third direction that is substantially perpendicular to the first direction or the second direction, and
a through hole provided in the third direction in a portion of the resonance space that is closer to the rear housing than to the window member,
wherein at least a portion of the resonance space is disposed to overlap the speaker diaphragm when the resonance space is viewed in the third direction.

2. The electronic device of claim 1, further comprising:
a support member coupled to the side member and formed to surround at least a portion of the speaker assembly.

3. The electronic device of claim 2, wherein:
the speaker assembly includes a first surface facing at least a portion of an inner surface of the side member and a second surface facing away from the first surface, and
the support member includes a first portion in which a third surface facing at least a portion of the inner surface of the side member and a fourth surface facing at least a portion of the first surface are disposed, and a second portion extending from the first portion and surrounding the speaker assembly.

4. The electronic device of claim 3, further comprising:
a fixing member disposed on the speaker assembly and the support member so as to press at least a portion of the speaker assembly and the support member.

5. The electronic device of claim 2, wherein the side member includes:
a first inner surface facing the support member,
a second inner surface substantially perpendicular to the first inner surface,
a third inner surface extending from the second inner surface to the through hole, and
a fourth inner surface facing the second inner surface.

6. The electronic device of claim 1, wherein the display includes:
a second circuit board disposed in the second direction with respect to the window member;
a touch sensor disposed between the window member and the second circuit board,
a first bent unit extending from the touch sensor in the third direction and configured to electrically connect the touch sensor and the second circuit board to each other; and
a display panel disposed between the touch sensor and the second circuit board, and a second bent unit extending from the display panel in a fourth direction that is different from the third direction and configured to electrically connect the display panel and the second circuit board to each other.

7. The electronic device of claim 6, wherein the first bent unit at least partially overlaps the speaker assembly when the display is viewed in the first direction.

8. The electronic device of claim 6, further comprising:
a first circuit board on which a processor configured to control an operation of the electronic device is disposed,
wherein the second circuit board includes a third bent unit extending from the second circuit board in a fifth direction opposite to the fourth direction to electrically connect the first circuit board and the second circuit board to each other.

9. The electronic device of claim 6, wherein the third direction and the fourth direction are substantially perpendicular to each other.

10. An electronic device comprising:
a window member, at least a portion of which is substantially transparent;
a first circuit board;
a second circuit board;
a touch sensor disposed under the window member,
a first bent unit extending from the touch sensor in a first bending direction and configured to electrically connect the touch sensor to the second circuit board; and
a display panel disposed between the touch sensor and the second circuit board, and a second bent unit extending from the display panel in a second bending direction that is different from the first bending direction to electrically connect the display panel to the second circuit board.

11. The electronic device of claim 10, wherein the second circuit board includes a top surface coupled to the display panel, and a bottom surface coupled to the first bent unit and the second bent unit.

12. The electronic device of claim 11, wherein the first bent unit has a "U" shape, and
a groove corresponding to the first bent unit is formed in the bottom surface.

13. The electronic device of claim 10, wherein the first bending direction and the second bending direction are substantially perpendicular to each other.

14. The electronic device of claim 10 further comprising:
a processor disposed on the first circuit board and configured to control an operation of the electronic device,
wherein the second circuit board includes a third bent unit extending from the second circuit board in a third bending direction opposite to the second bending direction to electrically connect the first circuit board and the second circuit board to each other.

15. The electronic device of claim 10, wherein the display panel is formed of an unbreakable (UB) panel.

16. The electronic device of claim 6, wherein the display panel is formed of an unbreakable (UB) panel.

17. The electronic device of claim 1, wherein the side member further comprises:
at least one fastening groove protruding into the space; and
at least one fastener configured to secure the speaker assembly is secured to the at least one fastening groove.

18. The electronic device of claim 1, further comprising a microphone disposed within the space and opposite the through hole.

19. The electronic device of claim 8, further comprising a biometric sensor disposed between the first circuit board and the rear housing.

20. The electronic device of claim 10, further comprising:
a biometric sensor disposed below the first circuit board; and
a housing including the window member, a rear housing that is opposite the window member, and a side member surrounding a space between the window member and the rear housing, wherein the side member includes (i) a resonance space having a shape recessed from the space, and a through hole provided in a portion of the resonance space that is closer to the rear housing than to the window member.

* * * * *